(12) United States Patent
Cheng et al.

(10) Patent No.: US 7,432,394 B2
(45) Date of Patent: Oct. 7, 2008

(54) RESOLUTION OF α-(PHENOXY) PHENYLACETIC ACID DERIVATIVES WITH NAPHTHYL-ALKYLAMINES

(75) Inventors: Peng Cheng, Union City, CA (US); Jingyuan Ma, Sunnyvale, CA (US); Xin Chen, San Ramon, CA (US); Yan Zhu, Foster City, CA (US); Zuchun Zhao, Pleasanton, CA (US)

(73) Assignee: Metabolex, Inc., Hayward, CA (US)

( * ) Notice: Subject to any disclaimer, the term of this patent is extended or adjusted under 35 U.S.C. 154(b) by 0 days.

(21) Appl. No.: 11/525,201

(22) Filed: Sep. 20, 2006

(65) Prior Publication Data

US 2007/0073082 A1    Mar. 29, 2007

Related U.S. Application Data

(60) Provisional application No. 60/720,114, filed on Sep. 23, 2005.

(51) Int. Cl.
*C07C 59/56* (2006.01)

(52) U.S. Cl. ............... 562/472; 562/401; 562/405; 560/62

(58) Field of Classification Search ............ 562/472, 562/401, 405; 560/62
See application file for complete search history.

(56) References Cited

U.S. PATENT DOCUMENTS

| | | | |
|---|---|---|---|
| 3,517,050 A | 6/1970 | Bolhofer | |
| 5,817,867 A | 10/1998 | Li et al. | |
| 6,262,118 B1 | 7/2001 | Luskey et al. | |
| 6,613,802 B1 | 9/2003 | Luskey et al. | |
| 6,624,194 B1 | 9/2003 | Luskey et al. | |
| 6,646,004 B1 | 11/2003 | Luskey et al. | |
| 7,199,259 B2 * | 4/2007 | Daugs | 560/62 |
| 2003/0220399 A1 | 11/2003 | Luskey et al. | |
| 2004/0039053 A1 | 2/2004 | Luskey et al. | |
| 2005/0075396 A1 | 4/2005 | Luskey et al. | |
| 2007/0203243 A1 | 8/2007 | Daugs | |
| 2007/0270490 A1 | 11/2007 | Luskey et al. | |

* cited by examiner

*Primary Examiner*—Yvonne Eyler
*Assistant Examiner*—Sudhakar Katakam
(74) *Attorney, Agent, or Firm*—Townsend and Townsend and Crew, LLP

(57) ABSTRACT

The present invention provides a methods and compounds for producing an enantiomerically enriched α-(phenoxy)phenylacetic acid compound of the formula:

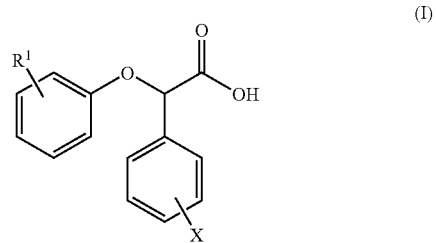

(I)

from a mixture of its enantiomers, where $R^1$ is alkyl or haloalkyl and X is halide.

21 Claims, No Drawings

RESOLUTION OF α-(PHENOXY) PHENYLACETIC ACID DERIVATIVES WITH NAPHTHYL-ALKYLAMINES

CROSS-REFERENCES TO RELATED APPLICATIONS

This application claims the benefit of U.S. patent application Ser. No. 60/720,114, filed Sep. 23, 2005, the content of which is incorporated herein by reference.

FIELD OF THE INVENTION

The present invention relates to an enantioselective resolution process for the separation of α-(phenoxy)phenylacetic acids from a mixture of enantiomers.

BACKGROUND OF THE INVENTION

Esters and amides derivatives of α-(phenoxy)phenylacetic acids, such as halofenate, are chiral compounds and are useful in ameliorating a variety of physiological conditions, including conditions associated with blood lipid deposition, Type II diabetes and hyperlipidemia (see, e.g., U.S. patent application Ser. No. 10/656,567 and U.S. Pat. No. 6,262,118 which is incorporated herein by reference in their entirety). α-(Phenoxy)phenylacetic acids contain a single chiral center at carbonyl carbon atom, and therefore exist in two enantiomeric forms.

Cytochrome P450 2C9 is an enzyme known to play a significant role in the metabolism of specific drugs. It is known to one skilled in the art that changes in drug metabolism mediated by inhibition of cytochrome P450 enzymes has a high potential to precipitate significant adverse effects in patients. It is also known that a racemic α-(phenoxy)phenylacetic acid, e.g., halofenic acid, inhibits cytochrome P450 2C9 (see, e.g., U.S. patent application Ser. No. 10/656,567 and U.S. Pat. No. 6,262,118). Thus, administration of a racemic α-(phenoxy)phenyl-acetic acid, such as halofenic acid or its derivatives, can lead to a variety of drug interaction problems with other drugs, including anticoagulants, anti-inflammatory agents and other drugs that are metabolized by this enzyme. It has been found that the (−)-enantiomer of halofenic acid is about twenty-fold less active in its ability to inhibit cytochrome P450 2C9 compared to the (+)-enantiomer. Id. Thus, it is desirable to administer the (−)-enantiomer of halofenic acid or its derivatives which is substantially free of the (+)-enantiomer to reduce the possibility of drug interactions.

Therefore, there is a need for an efficient process for producing a product enriched in a desired enantiomer of a α-(phenoxy)phenylacetic acid, e.g., (−)-halofenic acid.

SUMMARY OF THE INVENTION

One aspect of the present invention provides a method for producing an α-(phenoxy)phenylacetic acid compound of the formula:

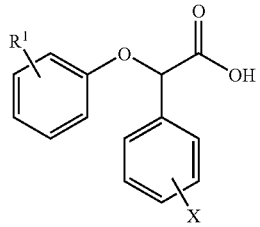

in an enantiomerically enriched form wherein
$R^1$ is alkyl or haloalkyl, and
X is halide;
from a mixture of the α-(phenoxy)phenylacetic acid compound comprising a first and a second enantiomer.

Methods of the present invention include:
(a) contacting a mixture of a first enantiomer and a second enantiomer of a compound of formula (I) with an enantiomerically enriched naphthylalkylamine under conditions sufficient to form a solid naphthylalkylammonium salt of said first enantiomer and decrease the ratio of the amount of free first enantiomer to the amount of free second enantiomer in the mixture; and
(b) separating the naphthylalkylammonium salt of the first enantiomer from the mixture;
(c) separating the naphthylalkylamine from the first enantiomer in the naphthylalkylammonium salt to produce enantiomerically enriched compound of formula (I).

In one particular embodiment, methods of the present invention include producing (−)-4-chloro-α-(3-trifluoromethylphenoxy)phenylacetic acid in an enantiomerically enriched form. In this embodiment the methods include:
(a) contacting a mixture of a first and second enantiomer of 4-chloro-α-(3-trifluoromethylphenoxy)phenylacetic acid with (S)-(−)-1-(2-naphthyl)ethylamine to form an ammonium salt; and
(b) separating the ammonium salt from the solution enriched in (+)-4-chloro-α-(3-trifluoromethylphenoxy)phenylacetic acid;
(c) separating (S)-(−)-1-(2-naphthyl)ethylamine from (−)-4-chloro-α-(3-trifluoromethylphenoxy)phenylacetic acid in the ammonium salt to produce enantiomerically enriched (−)-4-chloro-α-(3-trifluoromethylphenoxy)phenylacetic acid.

In another embodiment, compounds the formula (IV), (V) and (VI) are provided:

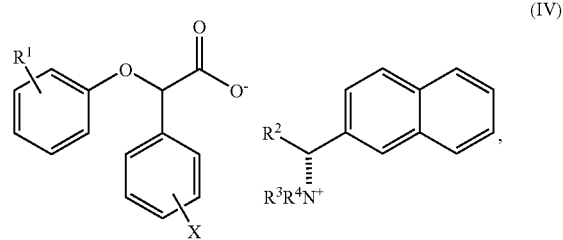

(IV)

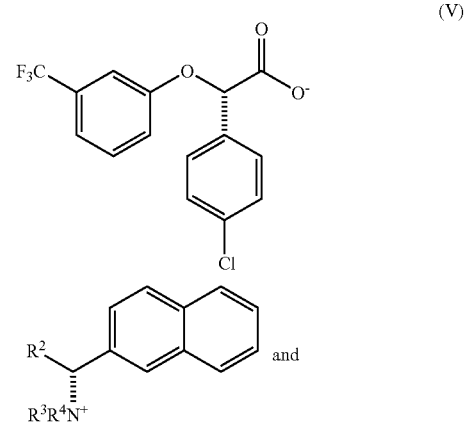

(V)

and

-continued

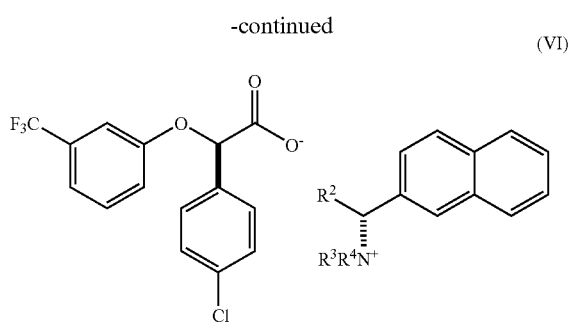

wherein
R² is alkyl; and
each of R³ and R⁴ is independently hydrogen or alkyl, or one of R³ or R⁴ is an amine protecting group.

One aspect of the present invention provides a method for enantioselectively producing a compound of the formula (VII):

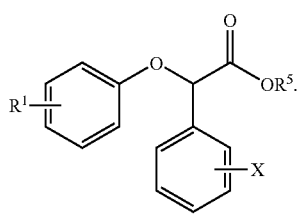

Methods of the present invention include:
(a) contacting a mixture of a first enantiomer and a second enantiomer of a compound of formula (I):

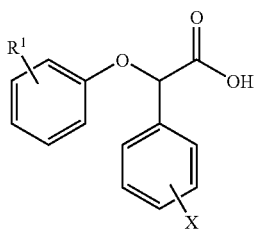

wherein
R¹ is alkyl or haloalkyl, and
X is halide;
with an enantiomerically enriched naphthylalkylamine under conditions sufficient to form a solid naphthylalkylammonium salt of said first enantiomer and decrease the ratio of the amount of free first enantiomer to the amount of free second enantiomer in the mixture; and
(b) separating the naphthylalkylammonium salt of the first enantiomer from the mixture
(c) separating the naphthylalkylamine from the first enantiomer in the naphthylalkylammonium salt to produce enantiomerically enriched compound of formula (I);
(d) contacting the enantiomerically enriched compound of formula (I) with a carboxylic acid activating reagent; and
(e) contacting the product of step (d) with a compound of the formula $(R^5O)_wM$ wherein
R⁵ is heteroalkyl;
M is hydrogen or a metal; and
the subscript w is the oxidation state of M; to produce the compound of formula (VII).

In one particular embodiment, methods of the present invention include enantioselectively producing a compound of the formula (VIII):

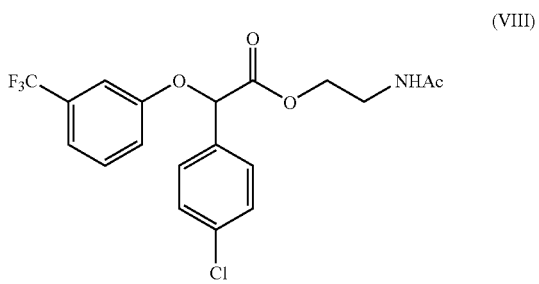

said method comprising:
(a) contacting a mixture of a first and second enantiomer of 4-chloro-α-(3-trifluoromethylphenoxy)phenylacetic acid with (S)-(−)-1-(2-naphthyl)ethylamine to form an ammonium salt; and
(b) separating the ammonium salt from the solution enriched in (+)-4-chloro-α-(3-trifluoromethylphenoxy)phenylacetic acid;
(c) separating (S)-(−)-1-(2-naphthyl)ethylamine from (−)-4-chloro-α-(3-trifluoromethylphenoxy)phenylacetic acid in the ammonium salt to produce enantiomerically enriched (−)-4-chloro-α-(3-trifluoromethylphenoxy)phenylacetic acid;
(d) contacting enantiomerically enriched (−)-4-chloro-α-(3-trifluoromethylphenoxy)phenylacetic acid with a carboxylic acid activating reagent selected from the group consisting of thionyl halides, anhydrides and thioester generating reagents; and
(e) contacting the product of step (d) with a HOCH₂CH₂NHAc to produce the compound of formula (VIII).

DETAILED DESCRIPTION

I. Definitions

"Alkyl" refers to straight or branched aliphatic hydrocarbons chain groups of one to ten carbon atoms, preferably one to six carbon atoms, and more preferably one to four carbon atoms. Exemplary alkyl groups include, but are not limited to, methyl, ethyl, n-propyl, 2-propyl, tert-butyl, pentyl, and the like.

"Naphthyl" refers to a monovalent bicyclic aromatic hydrocarbon moiety of 10 carbon ring atoms. Unless stated or indicated otherwise, a naphthyl group can be substituted with one or more substituents, preferably one, two, or three substituents, and more preferably one or two substituents selected from alkyl, haloalkyl, nitro, and halo. More specifically the term naphthyl includes, but is not limited to 1-naphthyl, and 2-naphthyl, and the like, each of which is optionally substituted with one or more substituent(s) discussed above.

"Chiral" or "chiral center" refers to a carbon atom having four different substituents. However, the ultimate criterion of chirality is non-superimposability of mirror images.

The terms "CPTA" and "halofenic acid" are used interchangeably herein and refer to (4-chlorophenyl)(3-trifluoromethylphenoxy)acetic acid.

"Enantiomeric mixture" means a chiral compound having a mixture of enantiomers, including a racemic mixture. Preferably, enantiomeric mixture refers to a chiral compound having a substantially equal amounts of each enantiomers. More preferably, enantiomeric mixture refers to a racemic mixture where each enantiomer is present in an equal amount.

"Enantiomerically enriched" refers to a composition where one enantiomer is present in a higher amount than prior to being subjected to a separation process.

"Enantiomeric excess" or "% ee" refers to the amount of difference between the first enantiomer and the second enantiomer. Enantiomeric excess is defined by the equation: % ee=(% of the first enantiomer)−(% of the second enantiomer). Thus, if a composition comprises 98% of the first enantiomer and 2% of the second enantiomer, the enantiomeric excess of the first enantiomer is 98%-2% or 96%.

The terms "halide" and "halo" are used interchangeably herein and refer to halogen, which includes F, Cl, Br, and I, as well as pseudohalides, such as —CN and —SCN.

"Haloalkyl" refers to alkyl group as defined herein in which one or more hydrogen atoms have been replaced with halogens, including perhaloalkyls, such as trifluoromethyl.

"Halofenate" refers to 2-acetamidoethyl 4-chlorophenyl-(3-trifluoromethyl-phenoxy)acetate (i.e., 4-chloro-α-(3-(trifluoromethyl)phenoxy)benzeneacetic acid, 2-(acetylamino)ethyl ester or (4-chlorophenyl)(3-trifluoromethylphenoxy)acetic acid), 2-(acetylamino)ethyl ester).

"Heteroalkyl" means a branched or unbranched acyclic saturated alkyl moiety containing one or more heteroatoms or one or more heteroatom-containing substituents, where the heteroatom is O, N, or S. Exemplary heteroatom-containing substituents include =O, —OR$^a$, —C(=O)R$^a$, —NR$^a$R$^b$, —N(R$^a$)C(=O)R$^b$, —C(=O)NR$^a$R$^b$ and —S(O)$_n$R$^a$(where n is an integer from 0 to 2). Each of R$^a$ and R$^b$ is independently hydrogen, alkyl, haloalkyl, aryl, or aralkyl. Representative examples of heteroalkyl include, for example, N-acetyl 2-aminoethyl (i.e., —CH$_2$CH$_2$NHC(=O)CH$_3$).

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

The term "metal" includes Group I, II, and transition metals as well as main group metals, such as B and Si.

"Optical purity" refers to the amount of a particular enantiomer present in the composition. For example, if a composition comprises 98% of the first enantiomer and 2% of the second enantiomer, the optical purity of the first enantiomer is 98%.

Unless otherwise stated, the term "phenyl" refers to an optionally substituted phenyl group. Suitable phenyl substituents are same as those described in the definition of "aryl." Similarly, the term "phenoxy" refers to a moiety of the formula —OAr$^a$, wherein Ar$^a$ is phenyl as defined herein. Thus, the term "α-(phenoxy)phenylacetic acid" refers to acetic acid that is substituted on the 2-position with an optionally substituted phenyl and optionally substituted phenoxy moieties.

"Protecting group" refers to a moiety that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethylsilyl (TMS), 2-trimethylsilyl-ethanesulfonyl (SES), trityl and substituted trityl groups, alkyloxycarbonyl, 9-fluorenylmethyloxycarbonyl (FMOC), nitro-veratryloxycarbonyl (NVOC), and the like.

The term "rate" when referring to a formation of a salt refers to kinetic and/or thermodynamic rates.

As used herein, the term "treating", "contacting" or "reacting" refers to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "those defined above" and "those defined herein" when referring to a variable incorporates by reference the broad definition of the variable as well as preferred, more preferred and most preferred definitions, if any.

Many organic compounds exist in optically active forms, i.e., they have the ability to rotate the plane of plane-polarized light. In describing an optically active compound, the prefixes R and S are used to denote the absolute configuration of the molecule about its chiral center(s). The prefixes "d" and "l" or (+) and (−) are employed to designate the sign of rotation of plane-polarized light by the compound, with (−) or (l) meaning that the compound is "levorotatory" and with (+) or (d) is meaning that the compound is "dextrorotatory". There is no correlation between nomenclature for the absolute stereochemistry and for the rotation of an enantiomer. For a given chemical structure, these compounds, called "stereoisomers," are identical except that they are mirror images of one another. A specific stereoisomer can also be referred to as an "enantiomer," and a mixture of such isomers is often called an "enantiomeric" or "racemic" mixture. See, e.g., Streitwiesser, A. & Heathcock, C. H., INTRODUCTION TO ORGANIC CHEMISTRY, 2$^{nd}$ Edition, Chapter 7 (MacMillan Publishing Co., U.S.A. 1981).

The terms "substantially free of its (+)-stereoisomer," "substantially free of its (+)-enantiomer," are used interchangeably herein and mean that the compositions contain a substantially greater proportion of the (−)-isomer in relation to the (+)-isomer. In a preferred embodiment, the term "substantially free of its (+) stereoisomer" means that the composition is at least 90% by weight of the (−)-isomer and 10% by weight or less of the (+)-isomer. In a more preferred embodiment, the term "substantially free of its (+)-stereoisomer" means that the composition contains at least 99% by weight of the (−)-isomer and 1% by weight or less of the (+)-isomer. In the most preferred embodiment, the term "substantially free of its (+)-stereoisomer" means that the composition contains greater than 99% by weight of the (−)-isomer. These percentages are based upon the total amount of isomers in the composition.

The term "nucleation temperature" is the temperature where nuclei are first formed from a solution when solubility is lowered by for example, a) cooling, b) concentrating the solution or c) addition of an antisolvent.

The term "saturation point" is the point where the maximum amount of a substance is solubilized by a solution at a given temperature. It is an equilibrium condition.

The term "super saturation point" is the point where the amount of a substance in solution exceeds its solubility at a given temperature. It is not an equilibrium condition.

The term "saturation temperature" is a condition where two or more phases of a pure substance may exist together in equilibrium. A second phase need not actually be present. A phase is considered saturated as long as it is at a temperature where another phase could exist in equilibrium.

II. Introduction

While chiral synthesis has made an extensive progress in recent years, resolution of racemates still remains the method of choice in industrial process for preparation of optically active, i.e., chiral, compounds. Typically, a chiral compound is synthesized in a racemic form and the final product is resolved to yield an enantiomerically enriched compound.

This process of resolving the final product is particularly useful in a large scale preparation of pharmaceutically active chiral compounds. Although enantiomers of a chiral compound have exact same chemical bonds, the spatial orientation of atoms in enantiomers is different. Thus, one enantiomer of a chiral drug often exerts desired activity with a significantly less side-effect(s) than the other enantiomer. While such relationship between chirality of an optically active drug and its side-effect(s) has been known for sometime, many chiral drugs are still administered in a racemic form.

Diastereomeric crystallization is widely used on industrial scale. The theoretical once-through yield of a resolution via diastereomer crystallization is 50 percent. Typically, however, more than one re-crystallization process is necessary in order to produce a composition that is of a sufficient optical purity.

The present invention provides a method for enantiomerically enriching an enantiomeric mixture, preferably a racemic mixture, of α-(phenoxy)phenylacetic acid compound, e.g., halofenic acid. Preferably, methods of the present invention provides a solid acid-base salt of the (−)-enantiomer of α-(phenoxy)phenylacetic acid compound. In this manner, the (−)-enantiomer can be readily separated from the solution.

The carboxylic acid group of the enantiomerically enriched α-(phenoxy)phenylacetic acid can then be activated by a carboxylic acid activation group to produce an activated α-(phenoxy)phenylacetic acid, which can be reacted with an alcohol, an amine, a thiol, or other nucleophilic compounds to produce an enantiomerically enriched α-(phenoxy)phenylacetic acid esters, amides, thioesters, or other derivatives, respectively. Thus, enantiomerically enriched α-(phenoxy)phenylacetic acid compounds produced using methods of the present invention are useful in producing α-(phenoxy)phenylacetic acid derivatives such as those disclosed in U.S. patent application Ser. No. 10/656,567 and U.S. Pat. No. 6,262,118. In particular, methods of the present invention are useful in producing (−)-halofenate.

III. Enantioselective Crystallization

As noted above, most enantioselective crystallization processes require more than one re-crystallization process in order to produce a composition that is of a sufficient optical purity. However, present inventors have found that under certain conditions disclosed herein, α-(phenoxy)phenylacetic acid compound of a sufficient optical purity can be produced by a single crystallization process. Thus, in one aspect, methods of the present invention are based on the surprising and unexpected discovery by the present inventors that a mixture of a α-(phenoxy)phenylacetic acid compound can be enantiomerically enriched using a chiral naphthylalkylamine. In particular, methods of the present invention provide a desired enantiomer of the α-(phenoxy)phenylacetic acid compound in optical purity of at least about 95%, preferably at least about 96%, more preferably at least about 97% and most preferably at least about 97.5%.

In one embodiment, methods of the present invention provide enantiomeric enrichment of an mixture, preferably a racemic mixture, of a α-(phenoxy)phenylacetic acid compound of the formula (I):

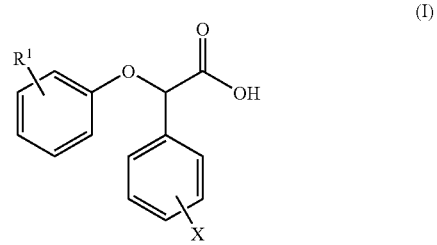

wherein $R^1$ is alkyl or haloalkyl, and X is halide. The process involves forming a solid enantiomerically enriched acid-base salt of the α-(phenoxy)phenylacetic acid compound using a chiral naphthylalkylamine.

In particular, methods of the present invention are directed to the resolution of α-(phenoxy)phenylacetic acid, e.g., halofenic acid (where $R^1$ is $CF_3$ and X is Cl), of the formula:

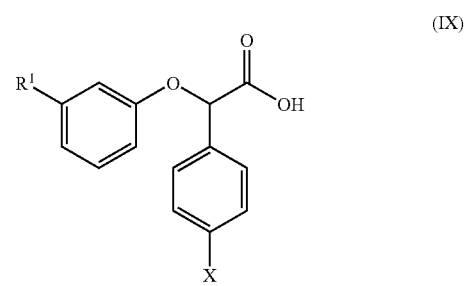

wherein $R^1$ is alkyl or haloalkyl, and X is halide.

In one particular embodiment, methods of the present invention are directed to the resolution of α-(phenoxy)phenylacetic acid of Formula I or, preferably of Formula IX, where X is chloro.

Yet in another embodiment, methods of the present invention are directed to the resolution of α-(phenoxy)phenylacetic acid of Formula I or, preferably, Formula IX, where $R^1$ is haloalkyl, preferably trifluoromethyl.

In one particular embodiment, methods of the present invention are directed to the resolution of 4-chloro-α-(3-trifluoromethylphenoxy)phenylacetic acid. Yet in another embodiment, methods of the present invention are directed to the resolution of the (−)-enantiomer of 4-chloro-α-(3-trifluoromethylphenoxy)phenylacetic acid.

In one particular embodiment, the α-(phenoxy)phenylacetic acid is crystallized using a chiral naphthylalkylamine. A wide variety of chiral naphthylalkylamines can be used, including those disclosed in the Examples section below.

Preferably, the chiral naphthylalkylamine used results in a solid acid-base salt of the (−)-enantiomer of α-(phenoxy)phenylacetic acid. In this manner, the (−)-enantiomer is readily separated from the solution, for example, by filtration. In one particular embodiment, the chiral naphthylalkylamines has the formula:

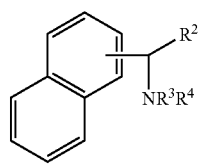

III wherein $R^2$ is alkyl; each of $R^3$ and $R^4$ is independently hydrogen or alkyl, or one of $R^3$ or $R^4$ is an amine protecting group.

In one particular embodiment, $R^2$ is methyl.

In another embodiment, $R^3$ and $R^4$ are hydrogen.

In still another the naphthylalkyl amine has the formula:

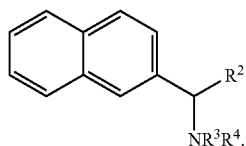

IV

In one embodiment, the chiral naphthylalkylamine is 1-(2-naphthyl)ethylamine and in another embodiment the chiral naphthylalkylamine is (S)-(−)-1-(2-naphthyl)ethylamine.

Still further, combinations of the preferred groups described above will form other preferred embodiments. For example, one particularly preferred chiral base is an naphthylalkylamine of Formula IV above, wherein $R^2$ is methyl and $R^3$ and $R^4$ are hydrogen; and a particularly preferred α-(phenoxy)phenylacetic acid compound is of Formula II above, wherein $R^1$ is trifluoromethyl and X is chloro. In this manner, a wide variety of preferred chiral bases and α-(phenoxy)phenylacetic acid compounds are embodied within the present invention.

The present inventors have found that the use of a chiral naphthylalkylamine in crystallization of the α-(phenoxy)phenylacetic acid has a significant effect on the optical purity of the enantiomeric enrichment, the ease of isolation and yield and stability of the α-(phenoxy)phenylacetic acid of Formula (I). For example, when a chiral naphthylalkylamine of the formula:

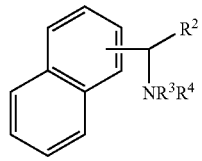

(wherein $R^2$, $R^3$ and $R^4$ are those defined herein) is used in crystallization of the α-(phenoxy)phenyl acetic acid compound of formula (I), higher overall yield of recovery is obtained in high % ee which is more stable, especially at higher pH (e.g. about 12 or higher) than other chiral bases. The chiral naphthylalkylamine is typically used with a non-chiral base such that a total of about one equivalent of base is used. The chiral naphthyl alkyl amine is typically used in an amount less than 0.5 molar equivalent, preferably about 0.48 molar equivalent or less, more preferably about 0.47 molar equivalent or less, and most preferably about 0.45 molar equivalent or less. It should be recognized that the chiral naphthylalkylamine itself should be of a sufficient enantiomeric purity in order to yield a highly enantiomerically enriched α-(phenoxy)phenylacetic acid derivatives. Examples of bases that may used with the chiral base, include, but are not limited to hydroxide, such as lithium hydroxide, potassium hydroxide, sodium hydroxide and the like; alkoxide, such as lithium alkoxide, potassium alkoxide, sodium hydroxide and the like; and the like; hydride, such as lithium hydride, potassium hydride, sodium hydride and the like; and the like.

The crystallization is typically conducted in solvents that allow for different solubilities of salts that are formed between two enantiomers of the α-(phenoxy)phenylacetic acid and the chiral naphthylalkylamine. In this manner, one of the diastereomeric salt precipitates out of the solution preferentially. Suitable crystallization solvents include protic solvents, such as water ($H_2O$) and alcohols and aprotic solvents, such as ethers. Examples of alcohol solvents, include but are not limited to ethanol and the like. Examples of ether solvents include, but are not limited to, t-butyl methyl ether (MTBE). In one particular embodiment, the α-(phenoxy)phenylacetic acid is crystallized using a combination of solvents, such as an alcohol solvent and a ether solvent. A particularly preferred crystallization solvent combination is water and MTBE.

The yield of enantiomerically enriched α-(phenoxy)phenyl acetic acid also depends on, among others, the amount of crystallization solvent used. For example, if a large quantity of crystallization solvent is used, the mixture becomes too dilute and the solid formation is reduced. If the amount of crystallization solvent used is too small, the solution will be supersaturated with the undesired diastereomeric salt which may lead to crystallization of the undesired diastereomeric salt, thereby reducing the optical purity of a desired enantiomer. Thus, when MTBE/$H_2O$ is used as the crystallization solvent, the amount of crystallization solvent used is preferably from about 2 grams to about 6 grams per one gram of the α-(phenoxy)phenylacetic acid compound, more preferably from about 3 grams to about 5 grams, still more preferably from about 3.5 grams to about 4.5 grams, and most preferably about 4 grams.

In one embodiment, the crystallization process involves heating the crystallization solution mixture to a temperature above the nucleation temperature of both enantiomers to dissolve substantially all of both enantiomers. For example, the crystallization solution is heated to a temperature in the range of from about 60° C. to the boiling point of the solution, preferably from about 70° C. to about 80° C. More preferably, the crystallization solution is heated to about 75° C. The solution can be heated prior to and/or after the chiral naphthylalkylamine is added. Heating is carried out until the solid materials are substantially completely dissolved, which typically ranges from about 0.5 to about 16 hours, preferably from about 1 to about 8 hours.

The crystallization solution is then cooled until it is about or below the nucleation temperature of the first diastereomeric salt, e.g., salt of (−)-enantiomer of the α-(phenoxy)phenylacetic acid, but preferably above the nucleation temperature of the second diastereomeric salt, e.g., salt of (+)-enantiomer of the α-(phenoxy)phenylacetic acid. This allows formation of a solid acid-base salt of the first enantiomer with the chiral naphthylalkylamine. Without being bound by any theory, it is believed that the use of a chiral naphthylalkylamine results in formation of an acid-base salt with one of the enantiomer at a significantly faster rate than formation of an acid-base salt of the other enantiomer. This rate may be due to kinetic and/or thermodynamic rate difference between the two enantiomers. As with a typical compound, the solubility profile of the α-(phenoxy)phenylacetic acid compound of the present invention has a higher solubility at a higher temperature. Therefore, cooling the crystallization solution to just above the nucleation temperature of the second diastereomeric salt affords a higher recovery yield of the solid first diastereomeric salt.

After the slurry is formed, the crystallization solution can be further cooled until the temperature of the solution is near or above the saturation point of the second diastereomeric salt. This prevents formation of a diastereomeric solid acid-base salt from the second enantiomer while increasing the formation of the diastereomeric solid acid-base salt of the first enantiomer.

The rate of cooling the crystallization solution may affect the optical purity of the solid acid-base salt that is formed. For example, if the crystallization solution is cooled too fast, the undesirable enantiomer may get trapped within the lattice of the solid acid-base salt of the desired enantiomer. However, a too slow cooling rate increases the production time and cost. Therefore, the crystallization solution should be cooled at a rate which minimizes the loss of optical impurity but at a rate sufficient to be economical. Typically, the crystallization solution cooling rate is from about 0.05° C./min to about 1° C./min, preferably from about 0.1° C./min to about 0.7° C./min, and more preferably from about 0.25° C./min to about 0.4° C. The crystallization solution is then maintained at above the saturation point of the solid acid-base salt of the second, i.e., undesired, enantiomer. Typically, the crystallization solution is maintained at this temperature for about 1 to about 72 hours, preferably from about 1 to about 48 hours, and more preferably from about 1 to about 30 hours.

As expected, using a small amount of chiral naphthylalkylamine allows selective formation of the solid acid-base salt of the first enantiomer. However, the resulting yield will correspondingly be small. Theoretically, the amount of yield of the desired enantiomer from a racemic mixture is 50%. Thus, if 0.5 molar equivalent of the chiral naphthylalkylamine is used, the theoretical yield is 50% of the total α-(phenoxy) phenylacetic acid (or 100% of the desired enantiomer). In order to be economically desirable, methods of the present invention provide at least about 50% yield of the desired enantiomer, preferably at least about 60%, more preferably at least about 70%, and most preferably at least about 75%. Assuming 100% selectivity, these yields correspond to adding about 0.25, 0.30, 0.35 and 0.375 molar equivalent of the chiral naphthylalkylamine, which represent a minimum amount of the chiral naphthylalkylamine that need to be added to the crystallization solution.

It is believed that the tendency for the second enantiomer to form a solid acid-base salt with the chiral naphthylalkylamine is one of the major causes for variability of conventional crystallization processes. Thus, by determining the supersaturation point of the second, i.e., undesired, enantiomer, one can minimize or prevent unpredictability of a solid acid-base formation of the second enantiomer. Supersaturation points can be readily determined by one skilled in the art, e.g., by a solubility experiment.

It should be noted that while methods of the present invention are discussed in reference to the enrichment of (−)-enantiomer that is present in the racemic mixtures, methods of the present invention are also applicable for enriching the (+)-enantiomer. The method of the present invention essentially provides a solid precipitate enriched in the (−)-enantiomer and a liquid filtrate, i.e., mother liquor, enriched in the (+)-enantiomer. Liberation of the desired (−)-enantiomer and recovery of the chiral naphthylalkylamine from the precipitated salt can be readily accomplished by acidification of the salt with, for example, a dilute mineral acid or any other inorganic or organic acid conventionally known to hydrolyze salts of this nature. While this procedure leaves the filtrate as an undesired by-product, the filtrate can be further treated with acid or, preferably, base to convert the (+)-enantiomer enriched filtrate to the racemic mixture. For example, the (+)-enantiomer can be racemized using aqueous sodium hydroxide solution. This racemic mixture can then be reused, i.e., recycled. In addition, the chiral naphthylalkylamine can also be recovered from the above described conversion step and recycled. Thus, the process of the present invention lends itself readily to a recycling-type of procedure.

IV. Synthesis of Racemic α-(phenoxy)phenylacetic Acid

One method of producing a racemic mixture of α-(phenoxy)phenylacetic acid of Formula I is shown in Scheme I below.

Scheme I

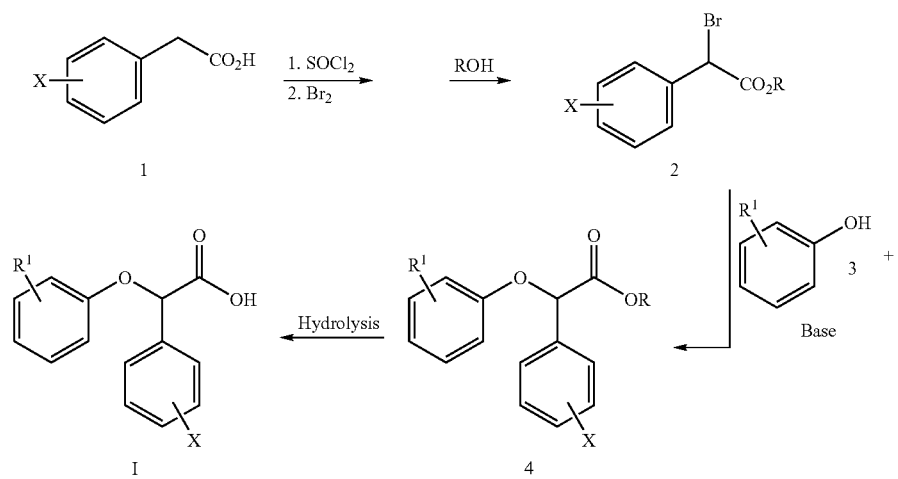

Thus, conversion of phenylacetic acid 1 to an activated carboxylic acid derivative, e.g., acid chloride, followed by α-bromination gave α-bromophenylacetyl chloride (not shown). The acid chloride was then converted to ester 2, where R is typically alkyl. Preferably, alcohol ROH, which is used to convert the acid chloride to ester 2, is the same alcohol that is used as a solvent in a subsequent reaction. In this manner, the number of different solvent types is minimized. In addition, by using the same ROH as the solvent in the subsequent reaction, the amount of by-product, e.g., by transesterification, formation is minimized. For example, isopropyl ester 2, i.e., where R is isopropyl, is particularly advantageous as the subsequent reaction is conveniently carried out in isopropanol solvent. A displacement reaction of ester 2 with a phenol compound 3 in the presence of a base, such as a hydroxide (e.g., potassium hydroxide), gave a α-(phenoxy)phenylacetic acid ester 4. Hydrolysis of α-(phenoxy)phenylacetic acid ester 4 afforded α-(phenoxy)phenylacetic acid I.

In this manner, (4-chlorophenyl)-(3-trifluoromethylphenoxy)-acetic acid, i.e., CPTA, can be prepared in five steps without intermediate isolation in about 85% yield following crystallization from heptane.

V. Utility of Enantiomerically Enriched α-(phenoxy)phenylacetic Acid

Enantiomerically enriched α-(phenoxy)phenylacetic acid compounds are useful intermediates in preparing a variety of pharmaceutically active compounds, including α-(phenoxy)phenylacetic acid compounds disclosed in U.S. patent application Ser. No. 10/656,567 and U.S. Pat. No. 6,262,118. Thus, another aspect of the present invention provides a method for enantioselectively producing a α-(phenoxy)phenylacetate compound of the formula (VII):

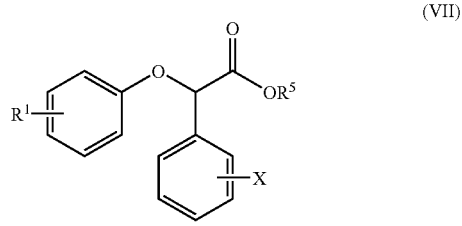

(VII)

from a racemic mixture of a α-(phenoxy)phenylacetic acid compound Formula I, wherein $R^1$ is alkyl or haloalkyl, X is halide and $R^5$ is heteroalkyl. Preferably the compound has the formula (VIII):

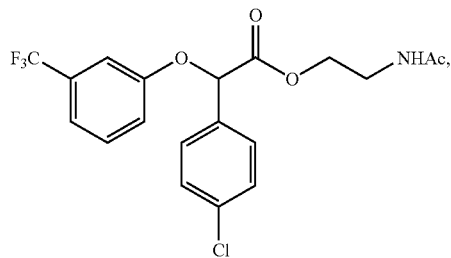

and more preferably the compound is (−)-halofenate. The method involves resolving the racemic mixture of the α-(phenoxy)phenylacetic acid compound of Formula I as described in embodiments above and contacting the enantiomerically enriched compound of formula (I) with a carboxylic acid activating reagent. Suitable carboxylic acid activating reagents include thionyl halides (e.g., thionyl chloride), anhydrides, thioester generating reagents, and other carboxylic acid activating reagents known to one skilled in the art.

The activated α-(phenoxy)phenylacetic acid is then reacted with a compound of the formula $(R^5—O)_wM$ to produce enantiomerically enriched α-(phenoxy)phenylacetate compound of Formula I, where $R^5$ is as defined above, M is hydrogen or a metal, e.g., Na, K, Li, Ca, Mg, Cs, etc. and the superscript w is the oxidation state of M. Preferably the compound of formula $(R^5—O)_wM$ is a N-acetyl ethanolamine derivative such as N-acetyl 2-aminoethyl (i.e., a moiety of the formula —$CH_2CH_2NHC(=O)CH_3$ or —$CH_2CH_2NHAc$). The present inventors have discovered that the reaction between the activated acid and the compound of formula $(R^5—O)_wM$ can be carried out without any significant racemization.

Additional objects, advantages, and novel features of this invention will become apparent to those skilled in the art upon examination of the following examples thereof, which are not intended to be limiting.

EXAMPLES

Reagents and Experimental Setup

Unless otherwise stated, reagents and solvents were purchased from Aldrich Chemical or Fisher Scientific. N-Acetylethanolamine was also obtained from Lancaster Synthesis. The racemic CPTA, i.e., halofenic acid was prepared according to the procedures disclosed in U.S. patent application Ser. No. 10/656,567 and U.S. Pat. No. 6,262,118. (S)-(−)-1-(2-naphthyl)-ethylamine was obtained from Lancaster.

Operations were conducted under a positive nitrogen atmosphere. A Camile process control computer attached to a recirculating heating and cooling system was used to regulate jacket temperatures in the jacketed straight-walled bottom-drain glass reactors. Unless otherwise indicated, solvents were removed using a Buchi rotary evaporator at 15 to 25 Torr with a bath temperature of up to 40° C. Solid samples were dried in a vacuum oven at 40° C., 15 to 25 Torr. A Cenco HYVAC vacuum pump was used to supply vacuum of less than 1 Torr for vacuum distillations. Water levels were determined by Karl Fisher analysis using a Metrohm 756 KF Coulometer and HYDRANAL Coulomat AG reagent. Melting points were determined using a Mettler Toledo FP62 melting point apparatus. pH was measured using a calibrated Orion Model 290A pH meter. Proton and $^{13}C$ NMR spectra were recorded on a Bruker Avance 300 MHz spectrometer.

Chiral HPLC analysis was carried out at λ=240 nm by injecting 10 μL of sample dissolved in mobile phase onto a (R,R)WHELK-O 1.5 μm 250×4.6 mm column (Regis Technologies) and eluting with a 1.0 mL/min flow of 95/5/0.4 (v/v/v) hexanes/2-propanol/acetic acid. For solid samples of the CPTA/(S)-(−)-1-(2-naphthyl)-ethylamine diastereomeric salt, the solid was added to aqueous hydrochloric acid and the CPTA was extracted into methylene chloride; after removing the solvent from the methylene chloride layer, the residue was dissolved in mobile phase for analysis.

Achiral HPLC analysis was carried out at λ=220 nm by injecting 5 μL of sample dissolved in mobile phase onto a Phenomenex LUNA 5 μm C18(2) 250×4.6 mm column at 25° C. A 1.5 mL/min flow of the gradient starting at 66 vol % water/34 vol % acetonitrile/0.1 vol % trifluoroacetic acid and increasing linearly to 26 vol % water/74 vol % acetonitrile/0.1 vol % trifluoroacetic acid at 20 minutes was used.

For analysis of acidic solutions of esters, such as halofenate, acetonitrile was used as the injection solvent.

When determined, product concentrations for CPTA and halofenate were evaluated by HPLC assay using the external standard method and the achiral analysis procedure at sample concentrations of less than 2.5 mg/mL.

Example 1

This example shows representative results of chiral resolution screening in ethanol using a variety of chiral phenylalkyl amine bases with chiral naphthylalkylamine bases.

Previous resolution of CPTA has been reported in U.S. patent application Ser. No. 10/656,567 and U.S. Pat. No. 6,262,118, in which chiral alkylamine bases were used. The preparation of CPTA is also reported therein.

This example compares the results of resolving a racemic mixture of CPTA using a variety of different chiral phenyl alkylamine bases with chiral naphthylamine bases to obtain a solid enantiomerically enriched (−)-isomer. The method of the present invention allows the solid enantiomerically enriched (−)-CPTA to be readily isolated from the solution in higher enantiomeric purity.

Racemic CPTA was prepared by the potassium hydroxide hydrolysis of racemic halofenate. For chiral base screening, equal molar mixtures of chiral base and sodium hydroxide were mixed with two equivalents of CPTA in water in glass vials, and the solutions were heated to 100° C., and EtOH was added until all solids dissolved, allowed to stand undisturbed. After cooling to ambient temperature, the crystalline salt precipitate was isolated by filtration, and both the solid phase and mother liquor were analyzed by chiral HPLC to determine the enantiomeric composition of both streams. The results from the screen are shown in Table 1.

TABLE 1

Results from Chiral Base Screen in Water/EtOH for CPTA Resolution.

| Example | Base | Solvent | Temp °C. | Solid % (+) | % (−) |
|---|---|---|---|---|---|
| 1A | (phenyl-CH(OH)-CH(NH-CH3)-CH3) | Ethanol/H₂O | 22 | 25 | 75 |
| 1B | (phenyl-CH(NH₂)-CH₃) | Ethanol/H₂O | 22 | 33.3 | 66.7 |
| 1C | (H₂N-C₆H₄-CH(OH)-CH(NH₂)-CH₂OH) | Ethanol/H₂O | 22 | 10.5 | 89.5 |
| 1D | (phenyl-CH-NH-CH₂-phenyl) | Ethanol/H₂O | 22 | 4.5 | 95.5 |
| 1E | (phenyl-CH-NH-CH₂-(2-CF₃-phenyl)) | Ethanol/H₂O | 22 | 5 | 95 |
| 1F | (2-naphthyl-CH(NH₂)-CH₃) | Ethanol/H₂O | 22 | 2.5 | 97.5 |

Example 2

This example shows the result of resolving racemic CPTA with (S)-(−)-1-(2-naphthyl)-ethylamine.

The general crystallization procedure was to charge a 150-mL jacketed bottom-drain flask with 20 g (60 mmol) of CPTA and 2.10 g KOH in 80 ml of water and MTBE (1:1) at r.t. To this solution was added 4.66 g (27.3 mmol) of (S)-(−)-1-(2-naphthyl)-ethylamine as its free base. The mixture became clear as the base dissolved, was heated to reflux and then cooled to r.t. to give a slurry. No seeding was required to induce nucleation. The solids were collected by filtration, washed with 60 ml of water and 50 ml of MTBE and dried under vacuum to give 13.3 g (44% yield by mass balance, 88% of theoretical yield) of the CPTA salt (calculated yields are derived from a forced mass balance from the racemic CPTA feed, by knowing the crystal and mother liquor composition of (−)-CPTA and (+)-CPTA). Chiral HPLC analysis found 2.0 and 98.0 area % of (+) and (−)-CPTA, respectively, in the solid phase.

A crystallization is desirable for which isolation could be done near, preferably just above, the saturation temperature of the (+)-salt. At a loading of 4 g of solvent per gram of CPTA and with 0.45 equivalent of (S)-(−)-1-(2-naphthyl)-ethylamine, an isolation at room temperature appears to be very near the saturation level (or within the metastable zone) of the (+)-salt. These loadings of about 0.45 equivalent of (S)-(−)-1-(2-naphthyl)-ethylamine and about 4 g of water/MTBE per gram of CPTA provide a high purity (−)-salt (>98.0%) product, which can be used without a further recrystallization.

Example 3

This example shows a method for separating (−)-CPTA from the (S)-(−)-1-(2-naphthyl)-ethyl amine.

To separate (−)-CPTA from (S)-(−)-1-(2-naphthyl)-ethylamine, the diastereomeric salt is mixed with 1,2-dichloroethane, and aqueous hydrochloric acid is added to give a pH in the aqueous phase of less than about 2. After complete dissolution of the solid, the aqueous phase containing the hydrochloride salt of (S)-(−)-1-(2-naphthyl)-ethylamine is separated. After a water wash of the organic phase, the bulk of the 1,2-dichloroethane is removed by distillation to remove residual water. The pH of the combined aqueous phase was 0.9. HPLC assay of the organic phase found 99.8% of theory of (−)-CPTA as a solution in 1,2-dichloroethane. Complete solvent removal gave an oil.

Example 4

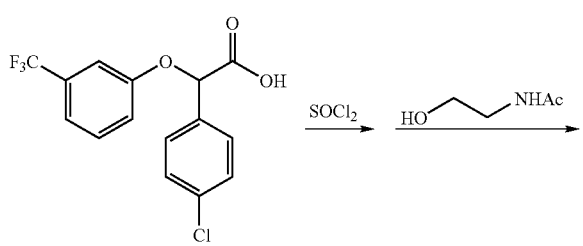

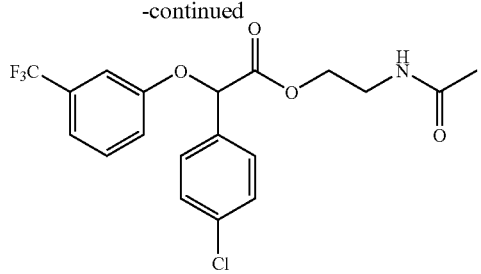

This example illustrates a method for preparing enantiomerically enriched (−)-halofenate without any significant racemization.

CPTA was prepared in five steps, as reported in U.S. patent application Ser. No. 10/656,567 and U.S. Pat. No. 6,262,118. Resolution gave an average of 44% yield (max 50%) of >98% optically pure (−)-CPTA diastereomeric salt. After removing the resolving agent, (−)-CPTA was reacted with thionyl chloride in 1,2-dichloroethane at reflux to yield a corresponding acid chloride. Reaction progress can be monitored by HPLC analysis. A small amount of distillate was removed to remove excess thionyl chloride. The mixture was cooled, and a large excess of vacuum distilled N-acetylethanolamine was added. Stirring at ambient temperature gave (−)-halofenate. The esterification reaction mixture was quenched by adding the reaction mixture to an aqueous potassium carbonate solution. (−)-Halofenate was isolated by solvent exchange and crystallization from the 6:1 heptane:2-propanol. First crop isolated yields ranged from 47 to 59% and averaged 55%. This isolated yield represents a reaction yield of 75 to 80% for this step. A second crop afforded a higher overall yield; however, the product quality was poorer with the second crop material. Molar accountability of the CPTA loaded, found as isolated halofenate, and halofenate and CPTA in the mother liquor, ranged from 90 to 99%.

By hydrolyzing the mother liquor residue with aqueous sodium hydroxide, (−)-CPTA can be recovered from the final product mother liquor and cycled back through the process. The resolving agent was isolated from water in about 90% recovery by a pH adjustment. Recovery and racemization of the (+)-CPTA using aqueous sodium hydroxide gave about 90% recovery. Overall, the first pass yield from 4-chlorophenylacetic acid was 21-23%. The entire eight-step process used three organic solvents, and three solid isolation steps.

Example 5

This example illustrates an alternative method for producing (−)-halofenate.

A 500-mL round-bottom flask with a magnetic stirrer is charged with 35.5 g (65.4 mmol) of the (−)-CPTA/(S)-(−)-1-(2-naphthyl)-ethylamine diastereomeric salt (98% ee), 89.0 g of 1,2-dichloroethane, and 35.5 mL of water. To the slurry is added 6.7 g (68 mmol) of 37% hydrochloric acid, and the mixture was stirred at ambient temperature to give two clear phases. The lower organic phase is removed and washed with 7.0 g of water. The organic phase is evaporated, then dissolved in 55.6 g of 1,2-dichloroethane and placed in a 250-mL round-bottom flask in a heating mantel with a magnetic stirrer and fitted with a reflux/distillation head. To the solution is added 7.5 mL (100 mmol) of thionyl chloride, and the solution is heated to reflux for 2 hours. Heating is continued to collect distillate. The solution is cooled to ambient temperature, then chilled in an ice bath for the addition of 25.85 g (251 mmol) of distilled N-acetylethanolamine (KF analysis 1176 and 1288 ppm water). The solution is added slowly with stirring to 9.90 g (71.6 mmol) of potassium carbonate in 36 g of water chilled in an ice bath. The reaction mixture is rinsed with 5 mL of 1,2-dichloroethane. The lower organic phase is removed and washed with 37 mL of water. The solution is evaporated to give an residue. The residue is treated with 54 g of heptane, and the solvent is removed to give a residue. To the residue is added 76 g of heptane, and the solvent is removed to give a residue. The residue is dissolved in 28 mL of 2-propanol at 40° C., then diluted with an additional 28 mL of 2-propanol and 334 mL of heptane. Cooling to ambient temperature gives a slurry which thickens upon cooling in an ice bath. After stirring for 2 hours, the solid is isolated by vacuum filtration, rinsed with 29 g of heptane, and dried to give (−)-halofenate.

Example 6

This example shows a method for recovering and recycling (+)-CPTA.

To recover and racemize the (+)-CPTA, the solvent from Example 4 was removed and replaced with 1,2-dichloroethane. Washing with water at a pH below about 2 removed the (S)-(−)-1-(2-naphthyl)-ethylamine for subsequent recovery. Aqueous sodium hydroxide was added, and the aqueous solution heated to reflux. The 1,2-dichloroethane was either removed by distillation prior to the addition of the basic solution, or by a phase separation following addition of the basic solution. An 89% yield of racemic CPTA was isolated from heptane after heating an aqueous solution for four hours with 1.4 molar equivalents of sodium hydroxide. Isolation of CPTA as a crystallized intermediate provided a more consistent quality feed for the resolution step.

Example 7

This example illustrates a method for recovering (S)-(−)-1-(2-naphthyl)-ethylamine.

(S)-(−)-1-(2-Naphthyl)-ethylamine is found in the acidic phase from separation of (−)-CPTA from the diastereomeric salt, and from the acidic wash step of the CPTA recovery from the resolution mother liquors. Basification with aqueous sodium hydroxide to a pH greater than about 12 results in good recovery.

Example 8

This example illustrates preparation and resolution of racemic CPTA from halofenate.

A 1-L round-bottom flask with an overhead stirrer was charged with 129.75 g (0.312 mol) of racemic halofenate, 325 g of water, and 32.6 g (0.408 mol) of 50% aqueous sodium hydroxide. The slurry was heated to 60° C. for 1 hour to give a solution, then cooled. At a temperature of 40° C., 328.5 g of 1,2-dichloroethane and 44 g (0.45 mol) of 37% hydrochloric acid were added, and the two-phase mixture was cooled to 29° C. The pH of the aqueous phase was 0.85. The organic phase was separated and washed with 250 mL of water, then evaporated to a residue of 118.2 g. 2-Propanol (149 g) was added, and evaporated to a residue of 131.2 g. The residue, containing theoretically 103.2 g of racemic CPTA based on the amount of halofenate loaded, was charged to a 1-L bottom-drain reactor with 33.10 g (0.1556 mol) of (S)-(−)-1-(2-naphthyl)-ethylamine and 400 g of 2-propanol. The mixture was warmed to 67° C. to give a light slurry, then cooled to 1° C. at 0.075° C./min. The mixture was chilled to −7° C., and the solid isolated by vacuum filtration and washed with 60 mL of 2-propanol. The 92.74-g wetcake was reloaded to the 1-L reactor along with 477 g of 2-propanol, and the mixture heated to 75° C. to give a solution. The solution was cooled to 5° C. at 0.5° C./min, and the crystallized solid isolated by vacuum filtration, rinsed with 60 mL of 2-propanol, and dried to give 51.81 g (0.0956 mol, 31% yield) of the (−)-CPTA-(S)-(−)-1-(2-naphthyl)-ethylamine diastereomeric salt.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for producing a compound of the formula (I):

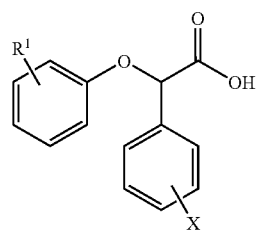

in an enantiomerically enriched form wherein
$R^1$ is alkyl or haloalkyl, and
X is halide;
said method comprising:
(a) contacting a mixture of a first enantiomer and a second enantiomer of a compound of formula (I) with at most about 0.5 molar equivalents of an enantiomerically enriched 1-(2-naphthyl)ethylamine under conditions sufficient to form a solid naphthylalkylammonium salt of said first enantiomer and decrease the ratio of the amount of free first enantiomer to the amount of free second enantiomer in the mixture;
(b) separating the naphthylalkylammonium salt of the first enantiomer from the mixture; and
(c) separating the naphthylalkylamine from the first enantiomer in the naphthylalkylammonium salt to produce compound of formula (I) in an optical purity of at least about 97.5% in at least about 75% yield.

2. The method of claim 1, wherein the naphthylalkylamine is (S)-(−)-1-(2-naphthyl)ethylamine.

3. A method for producing (−)-4-chloro-α-(3-trifluoromethylphenoxy)phenylacetic acid in an enantiomerically enriched form, said method comprising:
(a) contacting a mixture of a first and second enantiomer of 4-chloro-α-(3-trifluoromethylphenoxy)phenylacetic acid with (S)-(−)-1-(2-naphthyl)ethylamine to form an ammonium salt;
(b) separating the ammonium salt from the solution enriched in (+)-4-chloro-α-(3-trifluoromethylphenoxy)phenylacetic acid; and
(c) separating (S)-(−)-1-(2-naphthyl)ethylamine from (−)-4-chloro-α-(3-trifluoromethylphenoxy)phenylacetic acid in the ammonium salt to produce (−)-4-chloro-α-(3-trifluoromethylphenoxy)phenylacetic acid in an optical purity of at least about 97.5% in at least about 75% yield.

4. The method of claim 3, wherein said step (a) comprises contacting said mixture with at most about 0.5 molar equivalents of (S)-(–)-1-(2-naphthyl)ethylamine.

5. The method of claim 3, wherein said step (a) comprises contacting said mixture with at most about 1.0 molar equivalents of a combination of (S)-(–)-1-(2-naphthyl)ethylamine and a nonchiral base.

6. The method of claim 3, wherein said step (a) comprises contacting a mixture of a enantiomers of 4-chloro-α-(3-trifluoromethylphenoxy)phenylacetic acid with (S)-(–)-1-(2-naphthyl)ethylamine under conditions sufficient to produce a ratio of the amount of free (–)-4-chloro-α-(3-trifluoromethylphenoxy)phenylacetic acid to the amount of the free (+)-4-chloro-α-(3-trifluoromethylphenoxy)phenylacetic acid in the solution of at least from about 1:20.

7. The method of claim 3, wherein said step (a) comprises:
   (i) heating the mixture in a solvent to a temperature above the nucleation temperature of the first enantiomer; and
   (ii) lowering the solution temperature to a temperature about or below the nucleation temperature of (–)-4-chloro-α-(3-trifluoromethylphenoxy)phenylacetic acid to produce the ammonium salt of (–)-4-chloro-α-(3-trifluoromethylphenoxy)phenylacetic acid.

8. The method of claim 3, wherein step (a) is conducted in at most about 4 grams of solvent per gram of (–)-4-chloro-α-(3-trifluoromethylphenoxy)phenylacetic acid.

9. The method of claim 7, wherein the solvent is a member selected from the group consisting of water, ethanol, t-butyl methyl ether and a combination thereof.

10. The method of claim 7, wherein the solvent is a mixture of water and t-butyl methyl ether.

11. The method of claim 3, wherein said step (b) is conducted about or below the saturation point/temperature of the ammonium salt of the (+)-4-chloro-α-(3-trifluoromethylphenoxy)phenylacetic acid.

12. The method of claim 3, wherein step (c) further comprises recovering (S)-(–)-1-(2-naphthyl)ethylamine.

13. The method of claim 3 further comprising racemizing at least a portion of (+)-4-chloro-α-(3-trifluoromethylphenoxy)phenylacetic acid from the separated solution of step (b) by contacting the (+)-4-chloro-α-(3-trifluoromethylphenoxy)phenylacetic acid with a base.

14. The method of claim 13, wherein the mixture of the compound of formula (I) used in said step (a) comprises racemized (+)-4-chloro-α-(3-trifluoromethylphenoxy)phenylacetic acid.

15. A method for producing a compound of the formula (I):

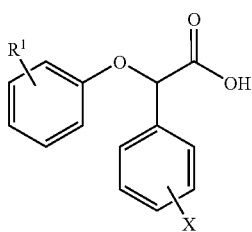

in an enantiomerically enriched form wherein
   R¹ is alkyl or haloalkyl, and
   X is halide;
said method comprising:
   (a) contacting a mixture of a first enantiomer and a second enantiomer of a compound of formula (I) with an enantiomerically enriched 1-(2-naphthyl)ethylamine under conditions sufficient to form a solid naphthylethylammonium salt of said first enantiomer and decrease the ratio of the amount of free first enantiomer to the amount of free second enantiomer in the mixture;
   (b) separating the naphthylethylammonium salt of the first enantiomer from the mixture;
   (c) separating the naphthylethylamine from the first enantiomer in the naphthylethylammonium salt to produce compound of formula (I) in an optical purity of at least about 97.5% in at least about 88% yield.

16. A method for producing (–)-4-chloro-α-(3-trifluoromethylphenoxy)phenylacetic acid in an enantiomerically enriched form, said method comprising:
   (a) contacting a mixture of a first and second enantiomer of 4-chloro-α-(3-trifluoromethylphenoxy)phenylacetic acid with (S)-(–)-1-(2-naphthyl)ethylamine to form an ammonium salt;
   (b) separating the ammonium salt from the solution enriched in (+)-4-chloro-α-(3-trifluoromethylphenoxy)phenylacetic acid;
   (c) separating (S)-(–)-1-(2-naphthyl)ethylamine from (–)-4-chloro-α-(3-trifluoromethylphenoxy)phenylacetic acid in the ammonium salt to produce (–)-4-chloro-α-(3-trifluoromethylphenoxy)phenylacetic acid in an optical purity of at least about 97.5% in at least about 88% yield.

17. The method of claim 15, wherein the solvent is a member selected from the group consisting of water, ethanol, t-butyl methyl ether and a combination thereof.

18. The method of claim 15, wherein the solvent is a mixture of water and t-butyl methyl ether.

19. A method for producing a compound of the formula (I):

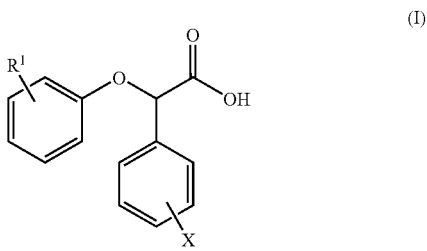

in an enantiomerically enriched form wherein
   R¹ is alkyl or haloalkyl, and
   X is halide;
said method comprising:
   (a) contacting a mixture of a first enantiomer and a second enantiomer of a compound of formula (I) with an enantiomerically enriched 1-(2-naphthyl)ethylamine in a mixture of water and t-butyl methyl ether under conditions sufficient to form a solid naphthylalkylammonium salt of said first enantiomer and decrease the ratio of the amount of free first enantiomer to the amount of free second enantiomer in the mixture;
   (b) separating the naphthylalkylammonium salt of the first enantiomer from the mixture;
   (c) separating the naphthylalkylamine from the first enantiomer in the naphthylalkylammonium salt to produce compound of formula (I) in an optical purity of at least about 97.5% in at least about 75% yield.

20. A method for producing (–)-4-chloro-α-(3-trifluoromethylphenoxy)phenylacetic acid in an enantiomerically enriched form, said method comprising:

(a) contacting a mixture of a first and second enantiomer of 4-chloro-α-(3-trifluoromethylphenoxy)phenylacetic acid with (S)-(−)-1-(2-naphthyl)ethylamine in a mixture of water and t-butyl methyl ether to form an ammonium salt;

(b) separating the ammonium salt from the solution enriched in (+)-4-chloro-α-(3-trifluoromethylphenoxy) phenylacetic acid; and (c) separating (S)-(−)-1-(2-naphthyl)ethylamine from (−)-4-chloro-α-(3-trifluoromethylphenoxy)phenylacetic acid in the ammonium salt to produce (−)-4-chloro-α-(3-trifluoromethylphenoxy)phenylacetic acid in an optical purity of at least about 97.5% in at least about 75% yield.

21. The method of claim 15 or 19, wherein said step (a) comprises contacting said mixture with at most about 0.5 molar equivalents of an enantiomerically enriched 1-(2-naphthyl)ethylamine.

* * * * *